US006179787B1

(12) United States Patent
Kelly et al.

(10) Patent No.: US 6,179,787 B1
(45) Date of Patent: Jan. 30, 2001

(54) COLLECTION CONTAINER ASSEMBLY

(75) Inventors: Karin E. Kelly, Los Angeles, CA (US); Donald J. Carano, Flanders; Gary R. Henniger, Wayne, both of NJ (US)

(73) Assignee: Becton Dickinson and Company, Franklin Lakes, NJ (US)

( * ) Notice: Under 35 U.S.C. 154(b), the term of this patent shall be extended for 0 days.

(21) Appl. No.: 08/928,286

(22) Filed: Sep. 12, 1997

(51) Int. Cl.[7] .......... A61B 5/00
(52) U.S. Cl. .......... 600/573; 206/216; 422/102
(58) Field of Search .......... 600/573; 422/102; 206/216, 140, 192, 570, 571, 572

(56) References Cited

U.S. PATENT DOCUMENTS

| | | | | |
|---|---|---|---|---|
| 2,717,661 | * | 9/1955 | Mayfield | 206/216 |
| 4,210,418 | | 7/1980 | Brown et al. . | |
| 4,401,434 | * | 8/1983 | Harris | 206/570 |
| 4,483,616 | | 11/1984 | Liston et al. | 356/246 |
| 4,578,588 | | 3/1986 | Galkin | 250/432 |
| 4,657,134 | * | 4/1987 | Woodworth et al. | 206/216 |
| 4,961,432 | * | 10/1990 | Guirguis | 600/573 |
| 4,980,129 | | 12/1990 | Columbus | 422/61 |
| 5,096,062 | | 3/1992 | Burkardt et al. | 206/361 |
| 5,167,929 | | 12/1992 | Korf et al. | 422/102 |
| 5,236,604 | | 8/1993 | Fiehler | 210/782 |
| 5,454,958 | | 10/1995 | Fiehler | 210/782 |
| 5,456,887 | | 10/1995 | Calvo et al. | 422/104 |
| 5,533,518 | | 7/1996 | Volger . | |
| 5,536,476 | | 7/1996 | Baxter | 422/102 |
| 5,665,280 | * | 9/1997 | Tropsha | 264/483 |
| 5,685,087 | * | 11/1997 | Flaugher et al. | 34/80 |

FOREIGN PATENT DOCUMENTS

| | | |
|---|---|---|
| 0 636 343 | 2/1995 | (EP) . |
| WO92 04978 | 4/1992 | (WO) . |

* cited by examiner

*Primary Examiner*—Cary O'Connor
*Assistant Examiner*—Pamela Wingood
(74) *Attorney, Agent, or Firm*—Nanette S. Thomas, Esq.

(57) ABSTRACT

The present invention is a collection container assembly comprising a container having a removable rounded bottom end and wherein the external dimensions of the container are substantially the same as a standard-sized blood collection tube but with a reduced internal volume.

3 Claims, 5 Drawing Sheets

COLLECTION CONTAINER ASSEMBLY

BACKGROUND OF THE INVENTION

1. Field of the Invention

This invention relates to a specimen collection container assembly and more particularly to a collection container for collecting biological fluid specimens where a small quantity of fluid may be collected and retained in the container while maintaining a container size sufficient to be easily accommodated and/or compatible with standard clinical equipment and instrumentation.

2. Description of Related Art

Blood samples and other biological fluid specimens are routinely taken and analyzed in hospital and clinical situations for various medical purposes. Collection, handling and testing of these samples typically requires the use of various medical testing instruments. As the blood and fluid specimens are usually collected in a standard sized collection tube, the medical instruments used to test the samples are designed to accommodate these standard sized collection tubes.

Conventional blood collection tubes used in most clinical situations are elongated cylindrical containers having one end closed by a semi-spherical or rounded portion and an opposed open end. The open end may be sealed by a resilient cap or stopper. The tube defines a collection interior which collects and holds the blood sample. The most common size of these blood collection tubes are designed to accommodate approximately about 2 ml to about 10 ml of blood or other biological fluid samples. Illustrative of such blood collection tubes is the VACUTAINER® brand blood collection tube sold by Becton, Dickinson and Company, 1 Becton Drive, Franklin Lakes, N.J. (registered trademark of Becton, Dickinson and Company).

A phlebotomist or other medical technician typically obtains a specimen of the patient's blood in the tube by techniques well known in the art. The tube is then appropriately labeled and transferred from the site of collection to a laboratory or other location where the contents of the tube are analyzed. During collection and analysis the tube may be supported by various medical instruments. The plasma or serum derived therefrom is processed and analyzed either manually, semiautomatically or automatically. In some cases, the specimen must first be dispensed from the collection tube to a sample test tube or cuvette.

In certain situations it is only necessary to obtain a small quantity of blood or other biological fluid specimens. These situations may include pediatric, or geriatric patients and other instances where large blood samples are not required. Small quantities of blood cannot be easily collected in standard collection tubes as described above because the sample level in such containers would not be adequate for retrieval prior to analysis. Such small quantities of fluids also have a tendency to significantly evaporate when stored in larger containers, thus concentrating the chemical and enzymatic constituents therein. This may result in erroneous analytical results and could possibly affect the diagnosis and treatment given to the patient. Therefore, it is desirable to employ small-volume containers which substantially inhibit evaporation for the storage and delivery of minute fluid samples in the laboratory.

Various specimen containers such as those incorporating a "false bottom" have been proposed to achieve decreased volume capacity in conjunction with standard external dimensions. However, these various specimen containers are not compatible with standard clinical equipment and instrumentation due to their design. In particular, these specimen containers have false bottoms with a generally flat, planar bottom end and a circular shaped opening.

Other specimen containers include partial-draw tubes which have standard external dimensions with partial evacuation so that blood fills only a portion of the internal volume. However, partial-draw tubes exhibit a reduction in the draw rate of a sample which reduces the collection efficacy of such tubes. In addition, partial-draw tubes may result in an inconsistent fill volume which may alter test results. Furthermore, it is difficult to determine accurate sample quantities with such partial-draw tubes because the slow rate of sample draw is not consistently measurable.

In clinical use, it is desirable for such specimen collection containers to have rounded bottom configurations that closely simulate a standard-sized blood collection tube configuration instead of planar bottoms. Rounded bottom configurations facilitate compatibility with clinical equipment and instrumentation.

Therefore there is a need to provide a specimen collection container assembly for collecting blood samples and other biological fluid specimens of relatively small volumes where the assembly may be accommodated and/or compatible with standard clinical equipment and/or instrumentation and where the integrity of the sample and specimens are maintained during draw, storage and transport.

SUMMARY OF THE INVENTION

The present invention is a collection assembly comprising a container. The container preferably comprises an open top portion, a bottom portion and a sidewall extending from the open top portion to the bottom portion. The bottom portion comprises a closed bottom end or true bottom and an annular skirt extending from the closed bottom end to a stop end at a lower bottom portion. The assembly further comprises an extension that may be secured and unsecured from the lower bottom portion of the container.

Most preferably, the extension comprises a top portion, a bottom portion, and a tubular column extending from the top portion to the bottom portion. The tubular column has an inner surface, an outer surface, an outer surface with ribs associated with the outer surface of the column. preferably, the extension further includes a flat shoulder between the tubular column and the bottom portion. Most preferably, the bottom portion is fully rounded or substantially semi-spherical in shape.

Alternatively, the tubular column may be a solid column having a solid inner core, an outer surface, and ribs associated with the outer surface.

The annular skirt of the container provides a false bottom effect to the assembly and the extension provides a means for allowing the container to be modified so as to be compatible with standard clinical equipment and instrumentation.

The extension is removably secured to the container whereby the tubular column is inserted into the annular skirt by force friction or fit. Thereby, the extension provides the assembly with a false bottom end that is rounded. The extension may be the same or different material than the container. The extension is removably unsecured from the container whereby the user slightly twists the container and the extension in opposite rotating directions thereby removing the extension from the container.

The true end may be the same or different material than the container and may be integral with the container or may be a discrete member. Additionally, the true end may be arcuate in shape to provide an internal volume for specimen collection having at least a partially rounded true bottom portion, or may be conical in shape.

In addition, the assembly may further comprise a closure such as a cap or a stopper at the open end of the container.

Preferably, the external dimensions of the assembly which includes the container and the extension, are about the same as a standard-sized or full draw blood collection container assembly. A standard-sized or full draw blood collection container assembly has an outer diameter of about 13 to about 16 millimeters, a length of about 75 to about 100 millimeters and an internal volume of about 6 to about 10 milliliters.

Most preferably, the assembly of the present invention can be either evacuated or non-evacuated. Desirably, the assembly is made from polyethylene terephthalate, polypropylene, polyethylene, polyethylene napthalate polyvinyl chloride or copolymers thereof.

An advantage of the assembly of the present invention is that it provides a full-draw blood collection container assembly having a reduced internal volume but with external dimensions about the same as a standard-sized blood collection container assembly.

A further advantage of the assembly of the present invention is that it provides a specimen collection container which is universally compatible with various clinical equipment and instrumentation.

The assembly of the present invention may be easily handled by equipment configured to handle standard-sized blood collection tubes having standard external dimensions.

Most notably, is that the assembly of the present invention provides a blood collection container having full draw external dimensions but with a reduced internal volume as compared to standard-sized full draw blood collection tubes The assembly of the present invention therefore addresses the need for a full-draw low-volume blood collection container assembly that presents the external dimensions of a standard-sized blood collection tube.

The assembly of the present invention may be used to reliably collect small samples of blood or biological fluids and to maintain the integrity of the samples during storage and transport as compared to using standard-sized blood collection tubes. In addition, the assembly of the present invention can also be accommodated by standard-sized blood collection, transportation, storage, and diagnostic equipment. Furthermore, the assembly of the present invention may be used to reliably collect small samples of blood or biological fluids without being under partial pressure.

Most notably, is that the assembly of the present invention provides a rounded bottom configuration that is substantially the same as a standard-sized blood collection tube with a fully rounded bottom. This particular feature in conjunction with all of the features of the container, distinguishes it from the specimen containers that have flat planar bottoms.

The assembly of the present invention is also compatible with existing instrumentation, labels, and bar code readers and obviates the need for new instrumentation and handling devices or procedures that would be required for smaller or varying sized tubes or tubes with flat planar bottoms.

DETAILED DESCRIPTION

The present invention may be embodied in other specific forms and is not limited to any specific embodiment described in detail which is merely exemplary. Various other modifications will be apparent to and readily made by those skilled in the art without departing from the scope and spirit of the invention. The scope of the invention will be measured by the appended claims and their equivalents.

Figure 1:
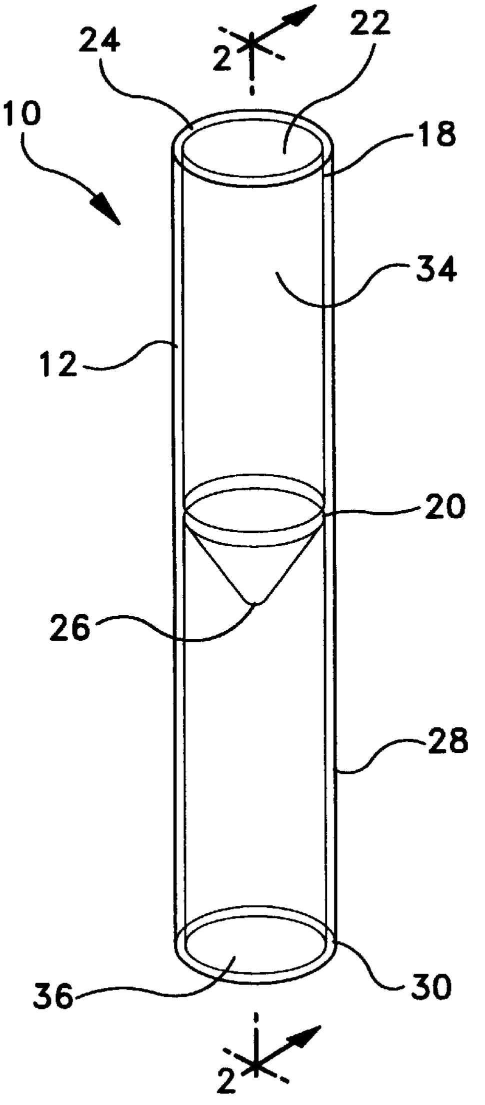
FIG-1 PRIOR ART
FIG. 1 is a perspective view of a false bottom specimen tube of the prior art.
Figure 2:
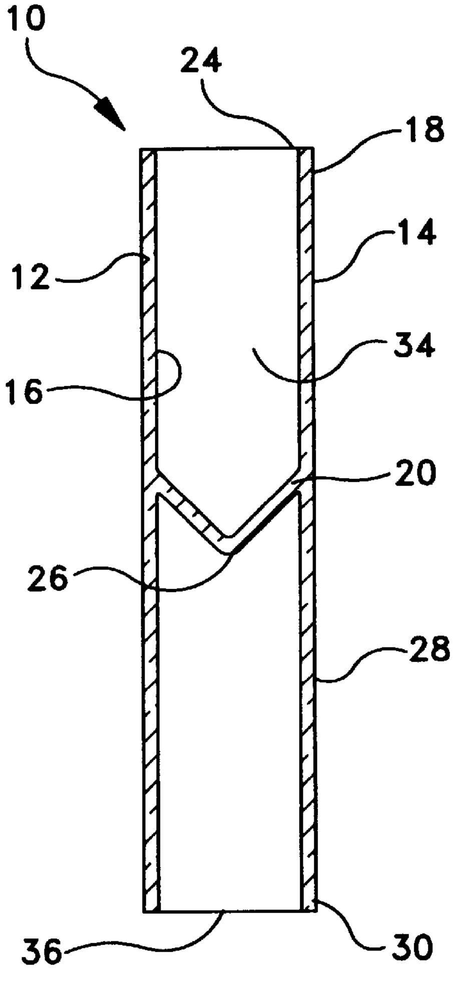
FIG-2 PRIOR ART
FIG. 2 is a longitudinal sectional view of the tube of FIG. 1 taken along line 2—2 thereof.

Referring to the drawings in which like reference characters refer to like parts throughout the several views thereof, FIGS. 1 and 2 show a false bottom specimen container 10 of the prior art, having a sidewall 12 having an outer surface 14 and an inner surface 16. Sidewall 12 extends from an upper portion 18 to a lower portion 20. Upper portion 18 includes an open end 22 and a rim 24. Lower portion 20 comprises a closed bottom end 26. An annular skirt 28 extends from to lower portion 20 and outer surface 14 to a flat planar bottom end 30 to define an open false bottom area 36. Interior volume 34 extends between rim 24 and closed bottom end 26.

Figure 3:
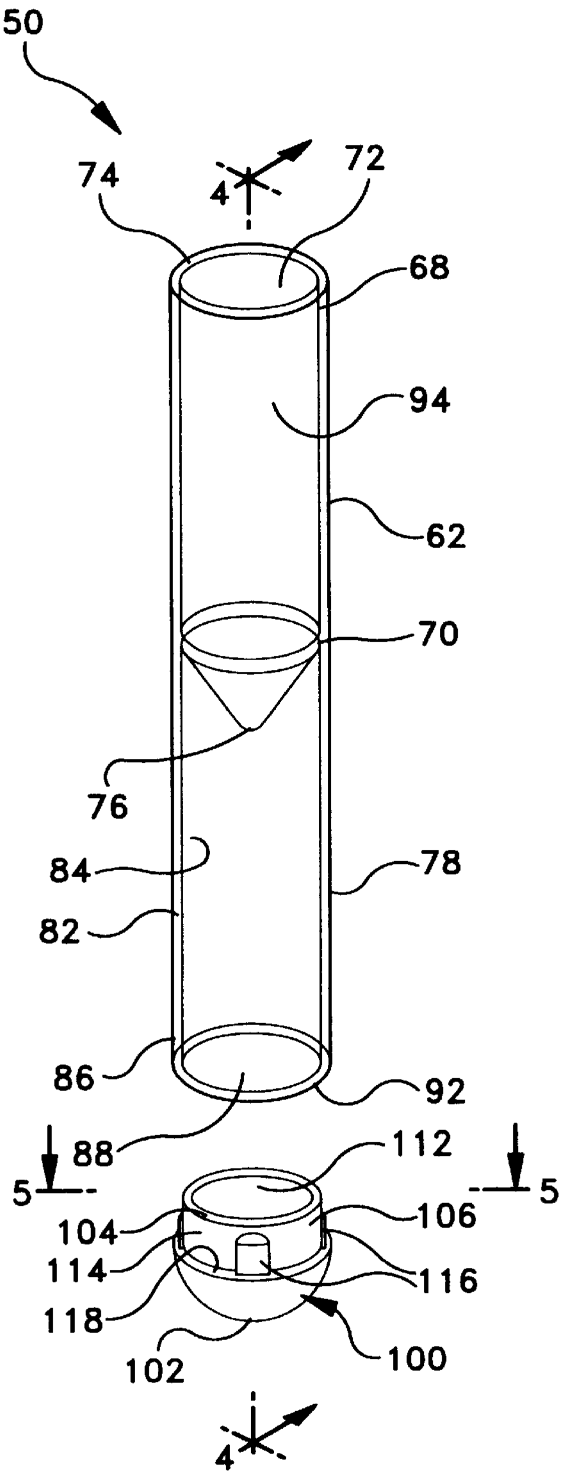
FIG. 3 is a perspective view of the assembly of the present invention with the extension unsecured from the container.
Figure 4:
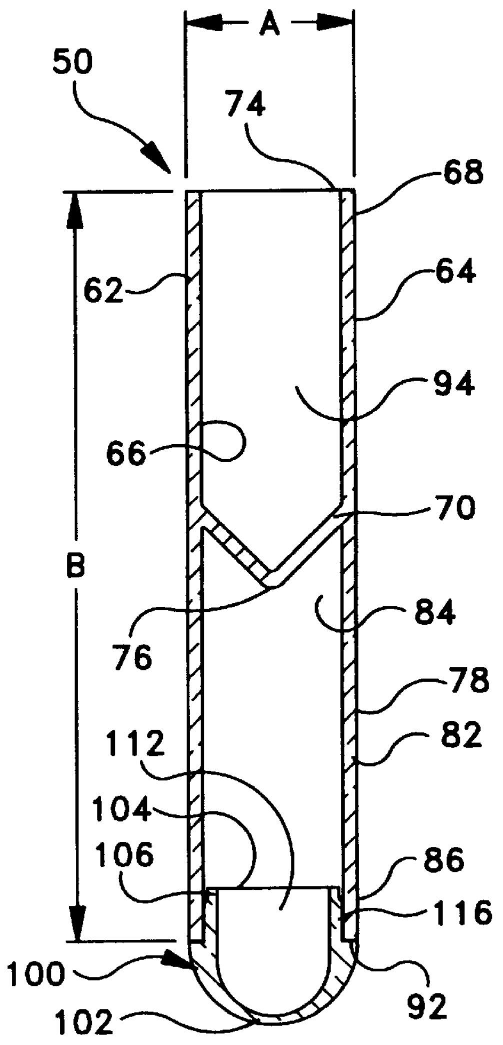
FIG. 4 is a longitudinal sectional view of the assembly of FIG. 3 taken along line 4—4 thereof with the extension removably secured to the bottom portion of the container.

Referring to the drawings in which like reference characters refer to like parts throughout the several views thereof, FIGS. 3 and 4 show the preferred embodiment of the present invention, assembly 50. Assembly 50 is false bottom a specimen container, having a sidewall 62 having an outer surface 64 and an inner surface 66. Sidewall 62 extends from an upper portion 68 to a lower portion 70. Upper portion 68 includes an open end 72 and a rim 74. Lower portion 70 comprises a closed bottom end or true bottom 76. An annular skirt 78 having an outer surface 82 and an inner surface 84, extends from lower portion 70 and outer surface 64 to a bottom end or false bottom end 86 to define an open false bottom area 88 and a planar rim surface 92 In addition, an extension 100 may be inserted into open false bottom area 88. An interior volume 94 extends between rim 74 and closed bottom end 76.

Closed bottom end 76 may be positioned at any point below rim 74 thus providing a variable interior volume 94. Closed bottom end 76 may be generally flat or planar in shape to provide a flat bottom surface for interior volume 94. Alternatively, closed bottom end 76 may be arcuate in shape to provide at least a partially rounded bottom surface for interior volume 94. Most preferably, closed bottom end is generally conical in shape to provide a conical, pointed bottom surface for interior volume 94. Additionally, closed bottom end 76 may be integral with sidewall 62 or may be a discrete member. Preferably closed bottom end 76 is integrally formed with sidewall 62.

Figure 5:
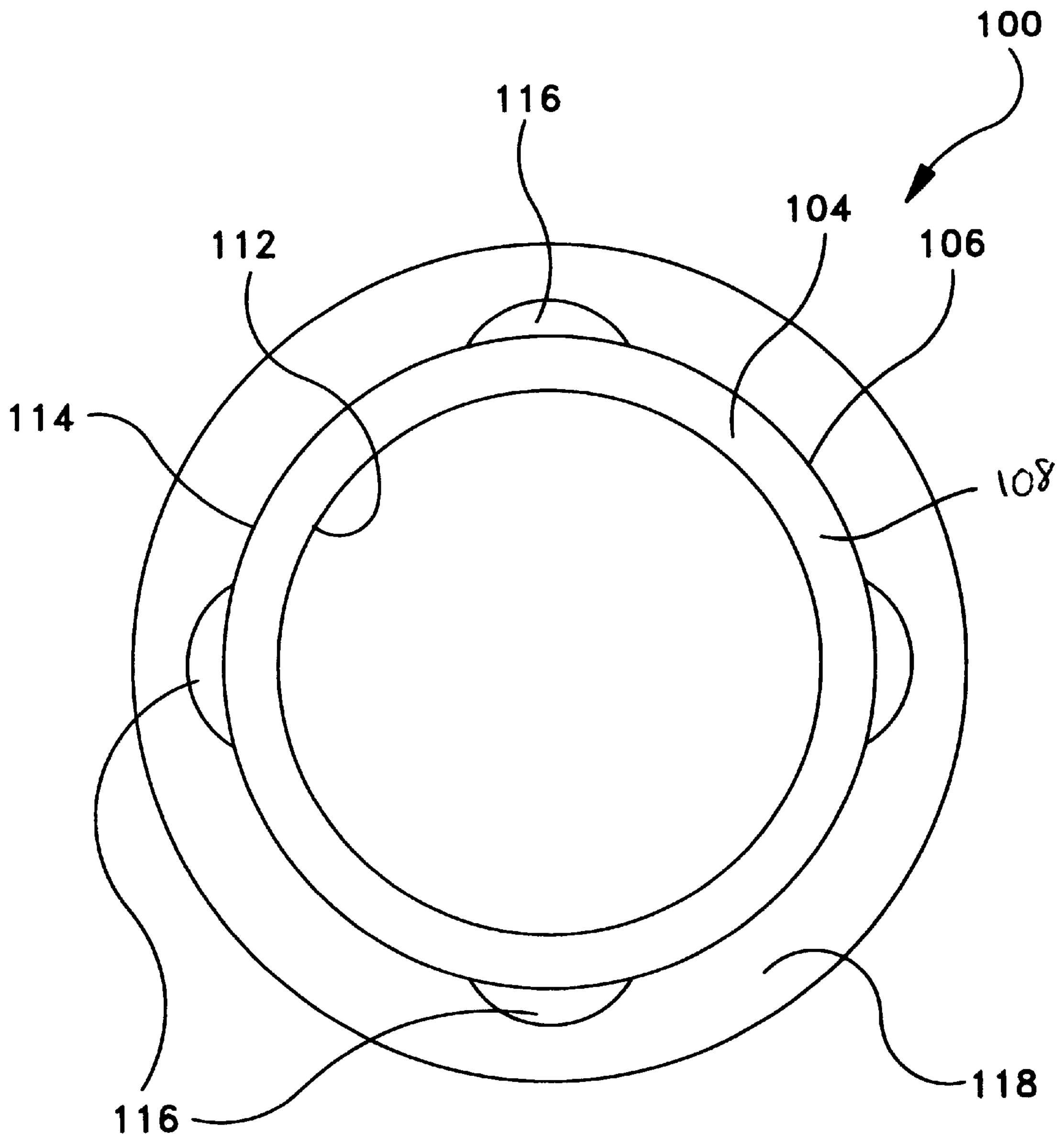
FIG. 5 is a top view of the extension of FIG. 3 taken along line 5—5 thereof.

As shown in FIGS. 3, 4, and 5, extension 100 includes a bottom portion 102, a top portion 104, and a column 106 extending from the bottom portion to the top portion. Column 106 may be tubular therefore comprising a sidewall 112 that includes an inner surface 112 and an outer surface

114, Although column 106 is shown as being tubular, it is within the purview of this invention that column 106 may be alternatively solid. A plurality of ribs 116 are associated on the outer surface 114. The extension further includes a flat shoulder surface 120 that separates the bottom portion from the column. Bottom portion 104 is fully rounded or substantially spherical in shape.

As shown in FIG. 4, assembly 50 has an outer diameter A of about 13 millimeters, a length B of about 75 millimeters, as measured from rim 74 to the bottom portion 102 of extension 100, and an interior volume 94 of about 1 to about 3 milliliters. It is within the purview of this invention that assembly 50 may have an outer diameter of about 13 to about 16 millimeters, a length of about 75 to about 100 millimeters and an interior volume of about 1 to about 3 millimeters.

Annular skirt 78 provides a means for allowing the container to be placed upright on a flat surface, as well as providing a means for converting the assembly with the extension to substantially the same external dimensions as a standard-sized blood collection tube.

Figure 6:
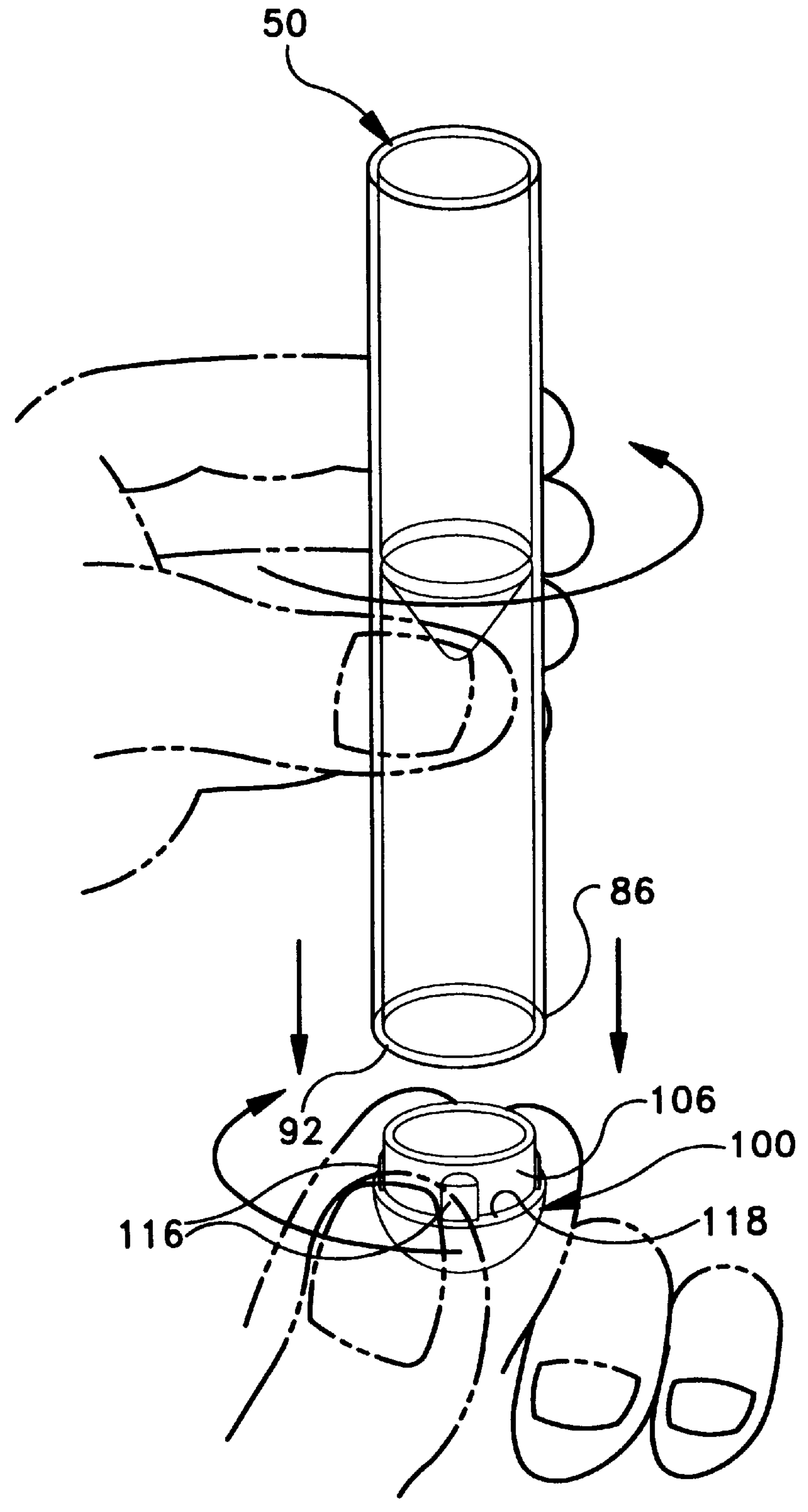
FIG. 6 illustrates the removal of the extension from the assembly.

As shown in FIGS. 4 and 6, extension 100 is readily compatible with open false bottom area 86. Open false bottom area 86 receives column 106 of the extension whereby inner surface 84 and ribs 106 provide an interference fit and flat shoulder surface 118 meets with planar rim surface 92.

As shown in FIG. 6, the extension may be removed from the assembly whereby the user slightly twists the container and the extension in opposite directions thereby removing the extension from the container.

Figure 7:
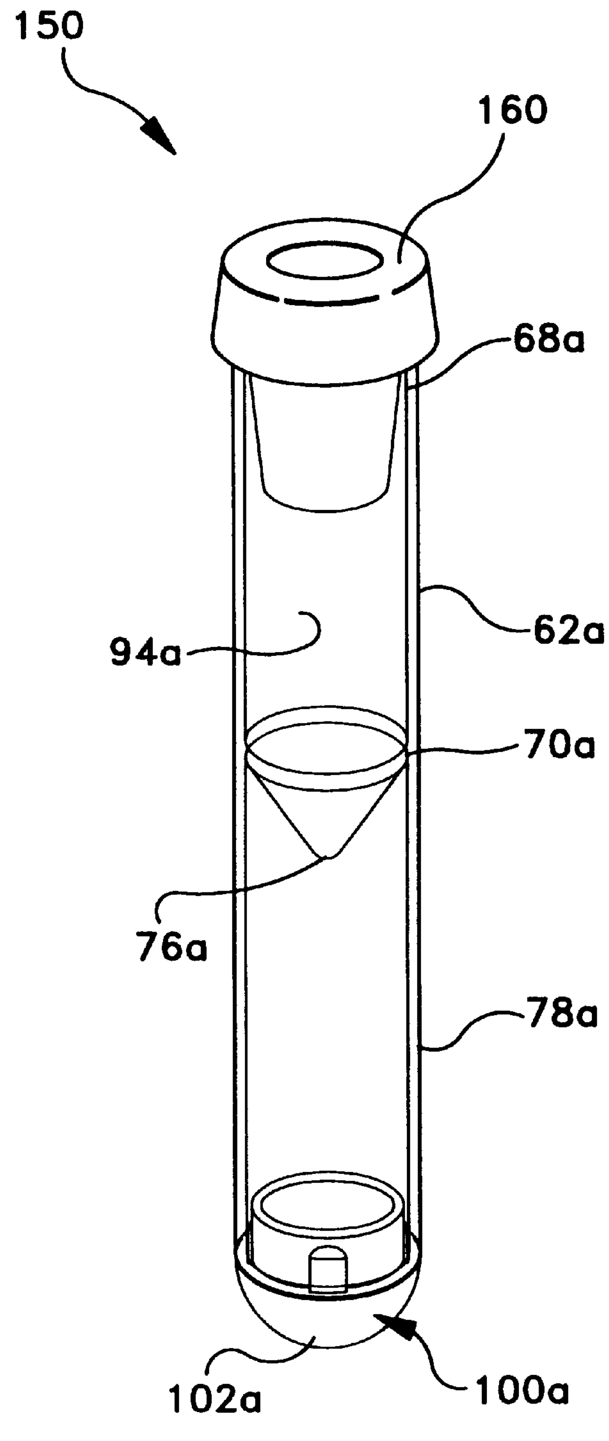
FIG. 7 is a perspective view of an alternate embodiment of the present invention.

The invention, as shown in FIG. 7 includes many components which are substantially identical to the components of FIGS. 3–4. Accordingly, similar components performing similar functions will be numbered identically to those components of FIGS. 3–4, except that a suffix "a" will be used to identify the similar components in FIGS. 7.

As illustrated in FIG. 7, a further embodiment of the invention is assembly 150 which includes a closure 160.

The embodiment of FIG. 7 may be evacuated or non-evacuated. When assembly 150 is evacuated, interior volume **94*a* is typically maintained at a lower-than-atmospheric internal pressure so that when a blood collection probe penetrates through the closure placing interior volume 94*a* in communication with the circulatory system of a patient, the lower-than-atmospheric pressure of interior volume 94*a* will draw blood from the patient into the tube. Assembly 150 may be described as a full-draw blood collection tube because the internal pressure of interior volume 94*a* is low enough to draw a volume of blood substantially equal to the volume of interior volume 94*a***.

What is claimed is:

1. A collection assembly comprising:

a container comprising an open top portion, a closed bottom portion, a sidewall extending from said top portion to said bottom portion, an annular skirt extending from said bottom portion to a second bottom portion comprising an outer surface and inner surface; and an extension removably connected to said container comprising a flat top portion, a rounded bottom portion, a column extending between said top portion and said bottom portion having an outer surface with ribs associated with said outer surface of said column and a flat shoulder between said column and said bottom portion whereby said inner surface of said annular skirt provides an interference fit with said ribs of said column and said flat shoulder meets with said second bottom portion of said annular skirt so that said extension may be removably secured with said container.

2. The assembly of claim 1, wherein said bottom portion of said container is arcuate in shape.

3. The assembly of claim 1, further comprising a closure in said open top portion of said container.

* * * * *